(12) United States Patent
Thompson-Nauman

(10) Patent No.: US 10,888,695 B2
(45) Date of Patent: Jan. 12, 2021

(54) OVER THE NEEDLE IMPLANT TOOLS AND IMPLANT TECHNIQUES UTILIZING SUCH TOOLS

(71) Applicant: Medtronic, Inc., Minneapolis, MN (US)

(72) Inventor: Amy E. Thompson-Nauman, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 324 days.

(21) Appl. No.: 14/961,999

(22) Filed: Dec. 8, 2015

(65) Prior Publication Data

US 2016/0158529 A1    Jun. 9, 2016

Related U.S. Application Data

(60) Provisional application No. 62/089,301, filed on Dec. 9, 2014.

(51) Int. Cl.
*A61N 1/05* (2006.01)
*A61N 1/39* (2006.01)
(Continued)

(52) U.S. Cl.
CPC ............. *A61N 1/05* (2013.01); *A61N 1/0504* (2013.01); *A61N 1/3956* (2013.01);
(Continued)

(58) Field of Classification Search
CPC .. A61N 1/0504; A61N 1/3956; A61N 1/0563; A61N 1/30; A61N 1/05–0597;
(Continued)

(56) References Cited

U.S. PATENT DOCUMENTS 4,629,450 A    12/1986    Suzuki et al.
4,832,687 A     5/1989    Smith, III
(Continued)

OTHER PUBLICATIONS

Engineering Tool Box, (2003). Young's Modulus—Tensile and Yield Strength for common Materials. [online] Available at: https://www.engineeringtoolbox.com/young-modulus-d_417.html [Accessed Jan. 9, 2019]. (Year: 2003).*

(Continued)

*Primary Examiner* — Kathleen S Holwerda
*Assistant Examiner* — Brooke Labranche

(57) ABSTRACT

Implant tools and techniques for implanting implantable medical leads or other implantable components in extracardiovascular locations, such as substernal locations, are described. In one example, the present application provides an implant tool for implanting a medical lead comprises a handle and a shaft. The shaft includes a proximal segment that is permanently coupled to the handle and a distal segment that is detachably coupled to the proximal segment. The distal segment includes a proximal end configured to couple to the proximal segment, a distal end, and a lumen extending an entire length of the distal segment from the proximal end to the distal end. In some instances, the implant tool may be part of a delivery system that includes a puncturing tool having a proximal end and a distal end, wherein the distal end is sharp, such as a syringe coupled to a needle.

22 Claims, 6 Drawing Sheets

(51) Int. Cl.
  *A61B 17/34* (2006.01)
  *A61B 17/32* (2006.01)
(52) U.S. Cl.
  CPC ....... *A61B 17/3415* (2013.01); *A61B 17/3468* (2013.01); *A61B 2017/320056* (2013.01); *A61N 1/0563* (2013.01)
(58) Field of Classification Search
  CPC ............ A61B 17/3415; A61B 17/3468; A61B 2017/320056
  See application file for complete search history.

(56) References Cited

U.S. PATENT DOCUMENTS

| | | | |
|---|---|---|---|
| 4,840,184 A * | 6/1989 | Garg | A61B 10/0283 600/566 |
| 5,300,106 A | 4/1994 | Dahl et al. | |
| 5,571,093 A * | 11/1996 | Cruz | A61M 25/0026 604/264 |
| 6,120,494 A | 9/2000 | Jonkman | |
| 6,405,733 B1 * | 6/2002 | Fogarty | A61B 90/39 128/899 |
| 6,436,068 B1 | 8/2002 | Bardy | |
| 6,605,094 B1 | 8/2003 | Mann et al. | |
| 7,194,309 B2 | 3/2007 | Ostroff et al. | |
| 7,792,591 B2 | 9/2010 | Rooney et al. | |
| 8,574,192 B2 | 11/2013 | Haarala et al. | |
| 8,715,244 B2 * | 5/2014 | Prechtel | A61M 39/0247 604/175 |
| 9,713,696 B2 * | 7/2017 | Yacoby | A61F 2/2436 |
| 2003/0088212 A1 * | 5/2003 | Tal | A61B 17/3415 604/163 |
| 2005/0033237 A1 * | 2/2005 | Fentress | A61M 25/0009 604/165.03 |
| 2005/0149097 A1 | 7/2005 | Regnell et al. | |
| 2008/0269716 A1 | 10/2008 | Bonde et al. | |
| 2008/0269763 A1 * | 10/2008 | Bonde | A61B 17/3468 606/99 |
| 2009/0030426 A1 * | 1/2009 | Zinn | A61B 17/3415 606/108 |
| 2009/0093833 A1 * | 4/2009 | Smith | A61B 17/3417 606/185 |
| 2009/0254019 A1 * | 10/2009 | Gehl | A61B 18/1477 604/21 |
| 2009/0254095 A1 | 10/2009 | Levine et al. | |
| 2010/0063512 A1 * | 3/2010 | Braga | A61B 17/32 606/108 |
| 2010/0174341 A1 | 7/2010 | Bolea et al. | |
| 2010/0318098 A1 | 12/2010 | Lund et al. | |
| 2012/0016377 A1 | 1/2012 | Geroy | |
| 2014/0025039 A1 * | 1/2014 | Rajendran | A61B 17/3401 604/512 |
| 2014/0066854 A1 | 3/2014 | Martin et al. | |
| 2014/0163655 A1 | 6/2014 | Chitre et al. | |
| 2014/0257186 A1 | 9/2014 | Kerr | |
| 2014/0330248 A1 | 11/2014 | Thompson-Nauman et al. | |
| 2015/0038949 A1 * | 2/2015 | Singh | A61M 39/0247 604/891.1 |
| 2015/0133951 A1 | 5/2015 | Seifert et al. | |
| 2015/0133952 A1 | 5/2015 | Seifert et al. | |
| 2015/0133953 A1 | 5/2015 | Seifert et al. | |
| 2015/0133954 A1 | 5/2015 | Seifert et al. | |

OTHER PUBLICATIONS (PCT/US2015/064430) PCT Notification of Transmittal of the International Search Report and the Written Opinion of the International Searching Authority, dated Mar. 14, 2016, 12 pages.
Medtronic, Inc., 6996SQ Subcutaneous, Unipolar Lead with Defibrillation Coil Electrode, Technical Manual, 2012, 22 pages.
Medtronic, Inc., 6996T Tunneling Tool, Technical Manual, 2011, 12 pages.
Greatbatch Medical, OptiSeal Valved Peelable Introducer Brochure, 2010, 2 pages.
Boston Scientific, EMBLEM™ S-ICD Subcutaneous Electrode Insertion Tool, Model 4711 User Manual, 2015, 28 pages.
Wikipedia, Seldinger Technique, http://en.wikipedia.org/wiki/Seldinger_technique, accessed Nov. 21, 2014, 3 pages.
International Preliminary Report on Patentability, dated Jun. 13, 2017, from International Application No. PCT/US2015/064430, filed Dec. 8, 2015, 7 pages.

* cited by examiner

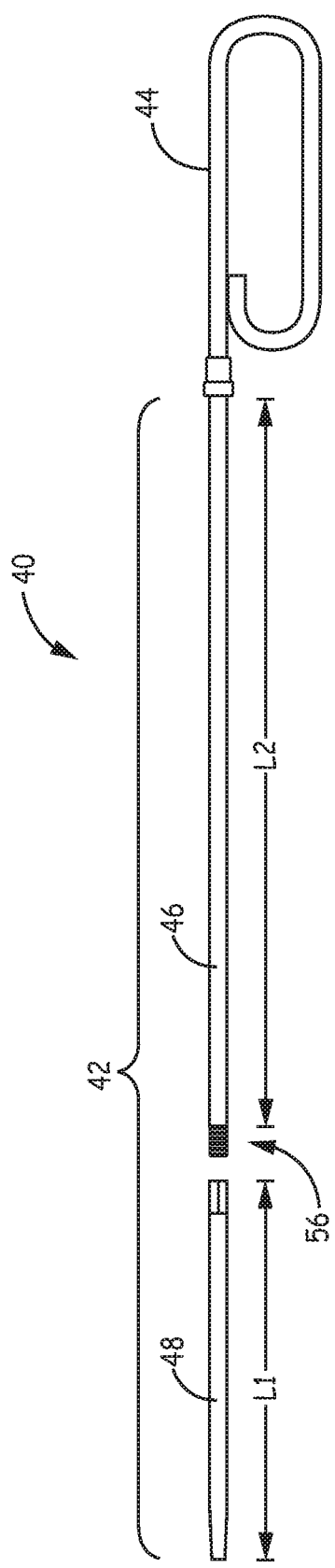
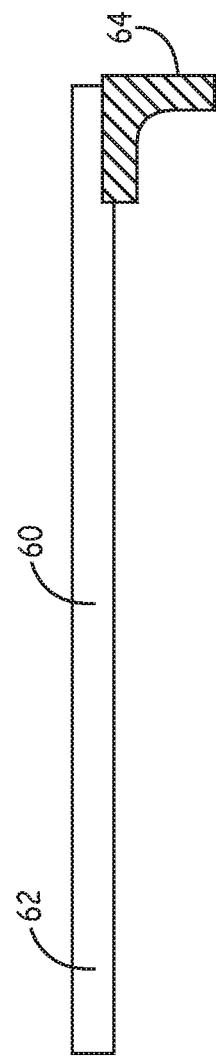

SECTION A-A'

SECTION B-B'

OVER THE NEEDLE IMPLANT TOOLS AND IMPLANT TECHNIQUES UTILIZING SUCH TOOLS

This application claims the benefit of U.S. Provisional Application No. 62/089,301, filed on Dec. 9, 2014, the entire content of which is incorporated herein by reference in its entirety.

TECHNICAL FIELD

The present application relates to implant tools and techniques for implanting implantable medical leads or other implantable components in extravascular locations utilizing such tools.

BACKGROUND

Implantable cardiac defibrillator (ICD) systems are used to deliver high energy electrical pulses or shocks to a patient's heart to terminate life threatening arrhythmias, such as ventricular fibrillation. Traditional ICD systems include a housing that encloses a pulse generator and other electronics of the ICD and is implanted subcutaneously in the chest of the patient. The ICD is connected to one or more implantable medical electrical leads that are implanted within the heart, referred to herein as transvenous leads.

Traditional ICD systems that utilize transvenous leads may not be the preferable ICD system for all patients. For example, patients with difficult vascular access may preclude placement of transvenous leads. As another example, children and other younger patients may also be candidates for non-transvenous ICD systems. Moreover, transvenous leads may become fibrosed in the heart over time, making lead revision and extraction procedures challenging.

A subcutaneous ICD system may be preferred for these patients. A subcutaneous ICD system includes a lead (or leads) that are implanted subcutaneously in the patient, i.e., between the skin and the ribs and/or sternum of the patient. As such, the subcutaneous ICD may eliminate the need to implant transvenous leads within the heart. Subcutaneous ICD systems may require an output of around 80 Joules (J) of energy to provide effective defibrillation therapy, approximately double that of ICD systems that utilize transvenous leads. As a result, subcutaneous ICDs may require larger batteries and more energy storage capacitors than transvenous ICDs, resulting in a device that is generally larger in size than transvenous ICDs. The large size of the subcutaneous ICD may compromise patient comfort, decrease system longevity and/or increase cost of the system. In addition, conventional subcutaneous ICD systems are incapable of delivering anti-tachycardia pacing (ATP) to the patient, which is a standard therapy in transvenous ICDs to terminate ventricular tachycardia without providing a shock.

SUMMARY

The present application relates to implant tools and techniques for implanting implantable medical leads or other implantable components in extracardiovascular locations utilizing such tools. As will be described in further detail herein, the implant tools are particularly useful in implanting leads (or other components) within a substernal location, e.g., under the sternum/ribcage in the anterior mediastinum.

In one example, the present application provides an implant tool for implanting a medical lead comprises a handle and a shaft. The shaft includes a proximal segment that is permanently coupled to the handle and a distal segment that is detachably coupled to the proximal segment. The distal segment includes a proximal end configured to couple to the proximal segment, a distal end, and a lumen extending an entire length of the distal segment from the proximal end to the distal end. In some instances, the implant tool may be part of a delivery system that includes a puncturing tool having a proximal end and a distal end, wherein the distal end is sharp, such as a syringe coupled to a needle.

In another example, the present application provides a method that includes traversing diaphragmatic attachments near a xiphoid process of a patient using a needle, placing the needle through a lumen of a removable distal segment of a shaft of a tunneling tool while the distal segment is removed from a proximal segment of the shaft of the tunneling tool, removing the needle from the distal segment of the shaft of the tunneling tool while leaving the distal segment such that a distal end of the distal segment is within the body of the patient and the proximal end of the distal segment extends outside the body of the patient, coupling the distal segment to the proximal segment, and tunneling the distal end of the distal segment along the posterior side of a sternum of the patient.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIG. 2 is a conceptual drawing illustrating an example tunneling tool that may be used to implant a medical lead, such as lead of FIG. 1, a catheter, or other implantable component.

FIG. 4 is a conceptual drawing of an example sheath that may be used in conjunction with the tunneling tool of FIG. 2 to implant the medical lead, catheter or other implantable component.

DETAILED DESCRIPTION

Figure 1A:
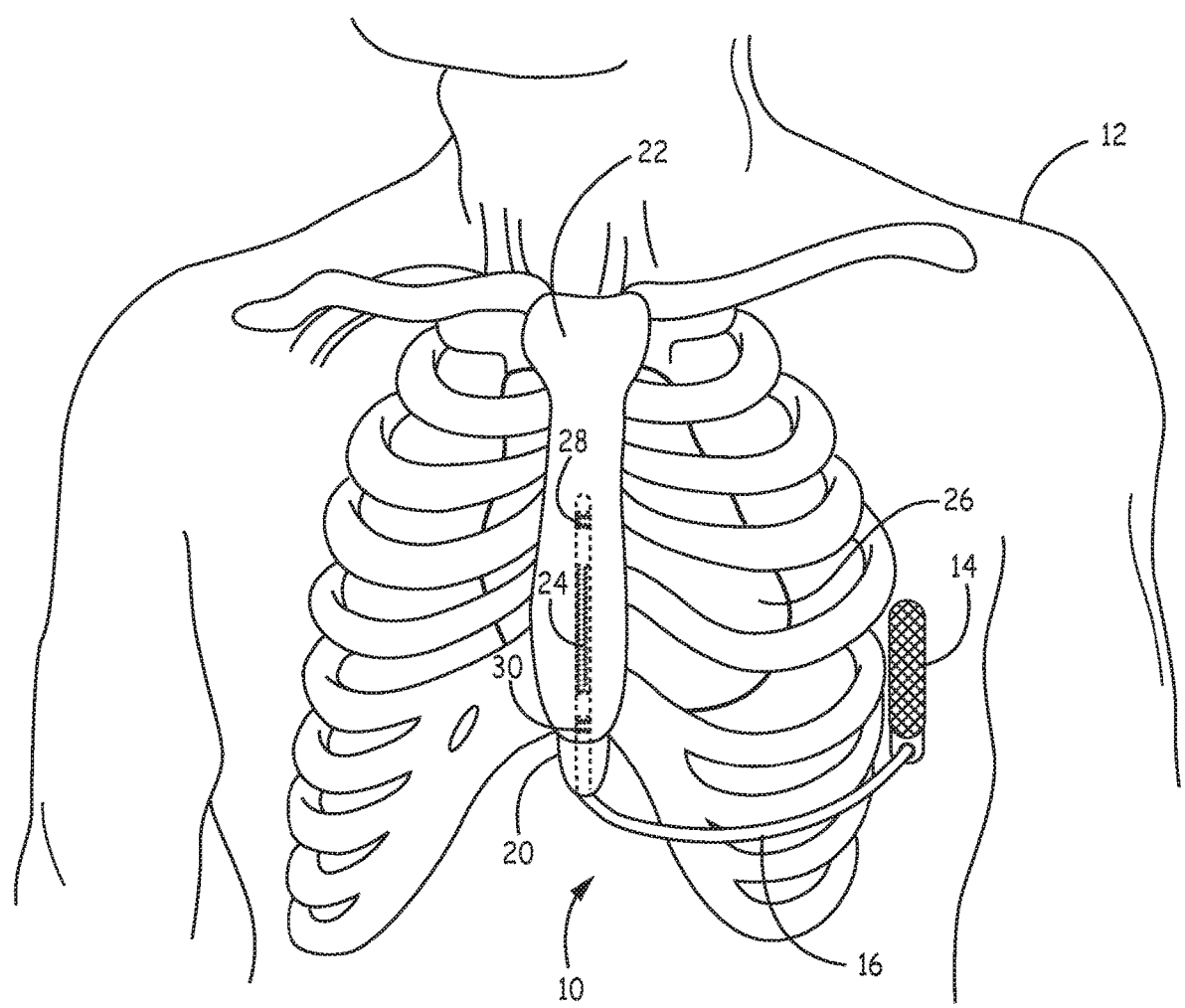
FIGS. 1A-C are conceptual diagrams illustrating various views of an example extravascular ICD system implanted within a patient.
Figure 1B:
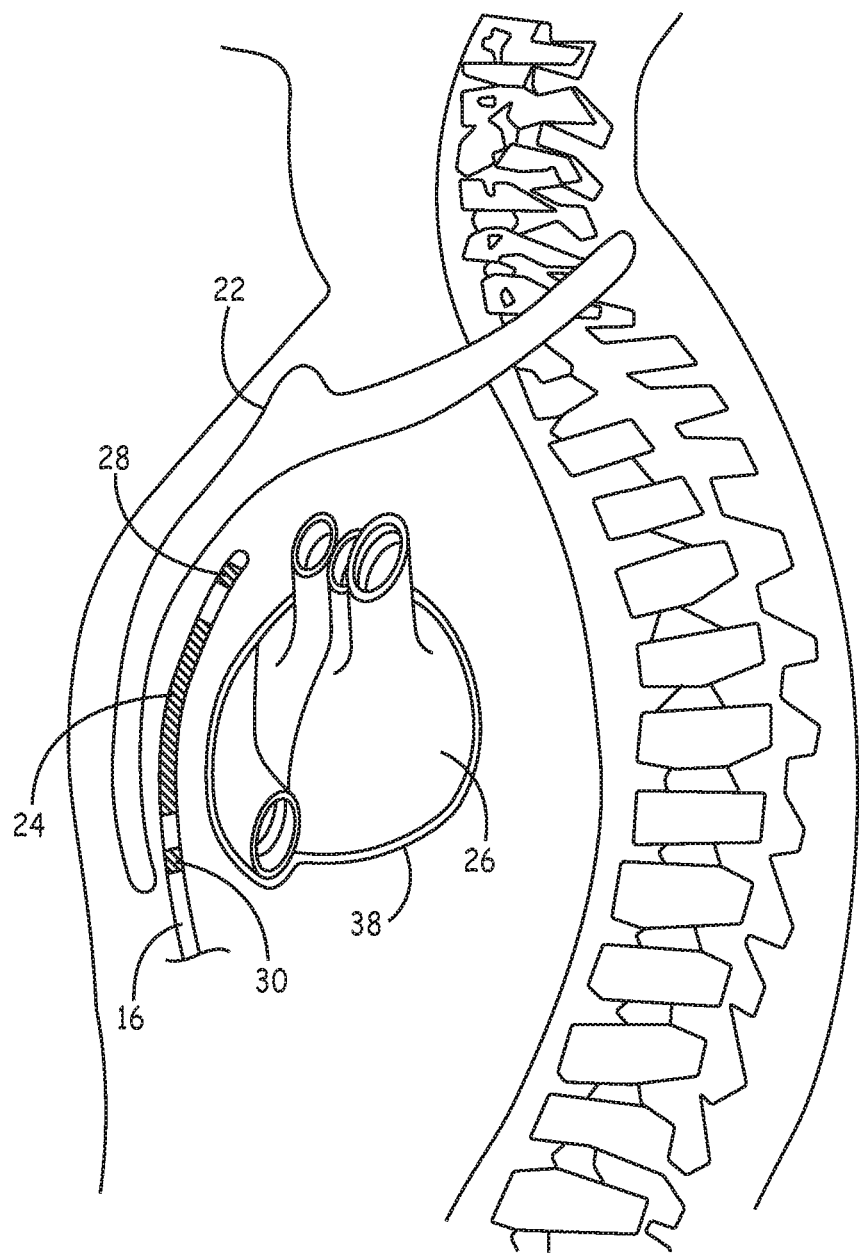
Figure 1C:
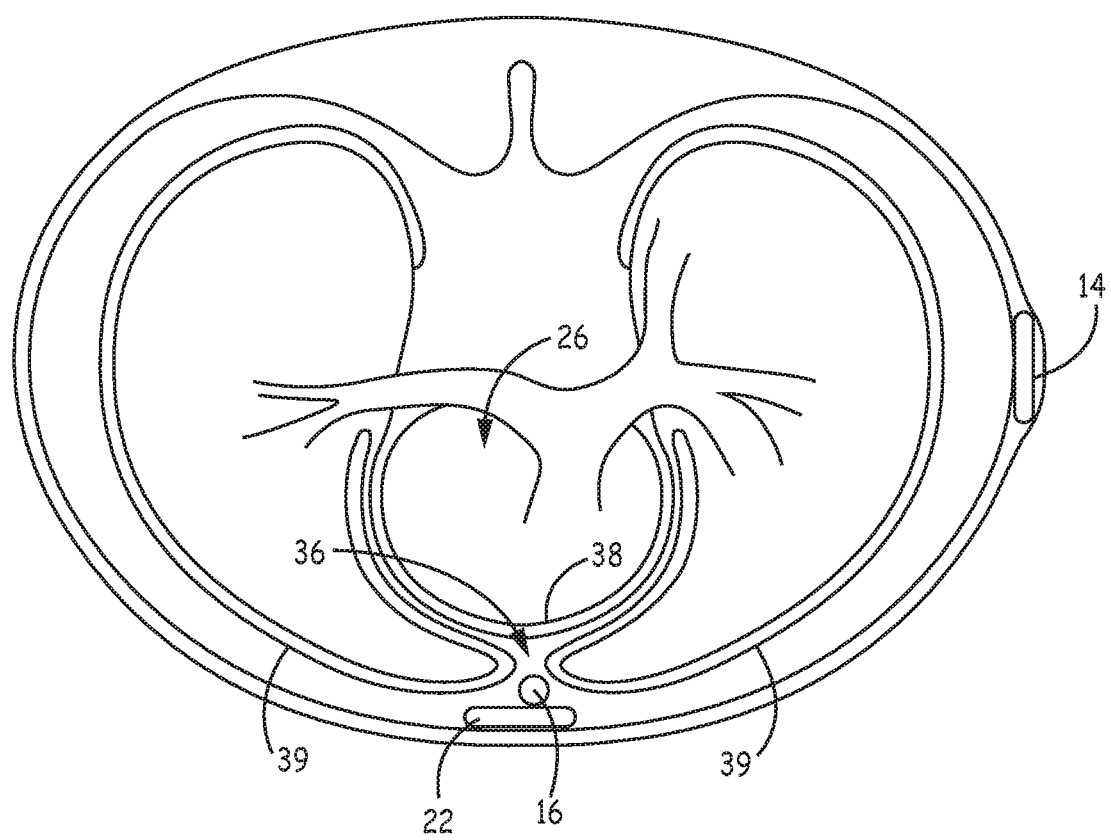

FIGS. 1A-C are conceptual diagrams of an implantable cardioverter-defibrillation (ICD) system 10 implanted within a patient 12. FIG. 1A is a front view of ICD system 10 implanted within patient 12. FIG. 1B is a side view of ICD system 10 implanted within patient 12. FIG. 1C is a transverse view of ICD system 10 implanted within patient 12. ICD system 10 includes an ICD 14 connected to a medical electrical lead 16. FIGS. 1A-C are described in the context of an ICD system capable of providing defibrillation and/or cardioversion shocks and, in some instances, pacing pulses. However, the techniques of this disclosure may also be used in the context of other implantable medical devices configured to provide other electrical stimulation therapies to the heart.

ICD 14 may include a housing that forms a hermetic seal that protects components of ICD 14. The housing of ICD 14 may be formed of a conductive material, such as titanium, or of a combination of conductive and non-conductive materials. The conductive material of the housing functions as a housing electrode. ICD 14 may also include a connector assembly (also referred to as a connector block or header) that includes electrical feedthroughs through which electrical connections are made between lead 16 and electronic components included within the housing. The housing may house one or more processors, memories, transmitters, receivers, sensors, sensing circuitry, therapy circuitry, power sources and other appropriate components.

ICD 14 is configured to be implanted in a patient, such as patient 12. ICD 14 is implanted subcutaneously on the left midaxillary of patient 12. ICD 14 is on the left side of patient 12 above the ribcage. ICD 14 may, in some instances, be implanted between the left posterior axillary line and the left anterior axillary line of patient 12. ICD 14 may, however, be implanted at other subcutaneous locations on patient 12 such as at a pectoral location or abdominal location.

Lead 16 includes an elongated lead body having a proximal end that includes a connector (not shown) configured to be connected to ICD 14 and a distal portion that includes electrodes 24, 28, and 30. The implant tools and techniques of this disclosure may be used to implant lead 16 as described herein. Lead 16 extends subcutaneously above the ribcage from ICD 14 toward a center of the torso of patient 12, e.g., toward xiphoid process 20 of patient 12. At a location near the center of the torso, lead 16 bends or turns and extends superior under/below sternum 22 within anterior mediastinum 36. Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 16 may be implanted substantially within the loose connective tissue and/or substernal musculature of anterior mediastinum 36.

In other embodiments, the distal portion of lead 16 may be implanted in other non-vascular, extra-pericardial locations, including the gap, tissue, or other anatomical features around the perimeter of and adjacent to, but not attached to, the pericardium or other portion of heart 26 and not above sternum 22 or ribcage. As such, lead 16 may be implanted anywhere within the "substernal space" defined by the undersurface between the sternum and/or ribcage and the body cavity but not including the pericardium or other portion of heart 26. The substernal space may alternatively be referred to by the terms "retrosternal space" or "mediastinum" or "infrasternal" as is known to those skilled in the art and includes the anterior mediastinum 36. The substernal space may also include the anatomical region described in Baudoin, Y. P., et al., entitled "The superior epigastric artery does not pass through Larrey's space (trigonum sternocostale)." Surg. Radiol. Anat. 25.3-4 (2003): 259-62. In other words, the distal portion of lead 16 may be implanted in the region around the outer surface of heart 26, but not attached to heart 26.

The distal portion of lead 16 may be implanted substantially within anterior mediastinum 36 such that electrodes 24, 28, and 30 are located near a ventricle of heart 26. For instance, lead 16 may be implanted within anterior mediastinum 36 such that electrode 24 is located over a cardiac silhouette of one or both ventricles as observed via an anterior-posterior (AP) fluoroscopic view of heart 26. In one example, lead 16 may be implanted such that a therapy vector from electrode 24 to a housing electrode of ICD 14 is substantially across the ventricles of heart 26. The therapy vector may be viewed as a line that extends from a point on electrode 24, e.g., center of electrode 24, to a point on the housing electrode of ICD 14, e.g., center of the housing electrode. However, lead 16 may be positioned at other locations as long as the therapy vector between electrode 24 and the housing electrode is capable of defibrillating heart 26.

In the example illustrated in FIGS. 1A-C, lead 16 is located substantially centered under sternum 22. In other instances, however, lead 16 may be implanted such that it is offset laterally from the center of sternum 22. In some instances, lead 16 may extend laterally enough such that all or a portion of lead 16 is underneath/below the ribcage in addition to or instead of sternum 22.

The elongated lead body of lead 16 contains one or more elongated electrical conductors (not illustrated) that extend within the lead body from the connector at the proximal lead end to electrodes 24, 28, and 30 located along the distal portion of lead 16. The elongated lead body may have a generally uniform shape along the length of the lead body. In one example, the elongated lead body may have a generally tubular or cylindrical shape along the length of the lead body. The elongated lead body may have a diameter of between 3 and 9 French (Fr) in some instances. However, lead bodies of less than 3 Fr and more than 9 Fr may also be utilized. In another example, the distal portion (or all of) the elongated lead body may have a flat, ribbon or paddle shape. In this instance, the width across the flat portion of the flat, ribbon or paddle shape may be between 1 and 3.5 mm. Other lead body designs may be used without departing from the scope of this disclosure. The lead body of lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead body of lead 16 may engage with respective ones of electrodes 24, 28, and 30. In one example, each of electrodes 24, 28, and 30 is electrically coupled to a respective conductor within the lead body. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 24, 28, and 30 and transmit sensed electrical signals from one or more of electrodes 24, 28, and 30 to the sensing module within ICD 14.

Defibrillation electrode 24 is illustrated in FIG. 1 as being an elongated coil electrode. Defibrillation electrode 24 may vary in length depending on a number of variables. Defibrillation electrode 24 may, in one example, have a length between approximately 5-10 centimeters (cm). However, defibrillation electrode 24 may have a length less than 5 cm and greater than 10 cm in other embodiments. Another example, defibrillation electrode 24 may have a length between approximately 2-16 cm.

In other embodiments, however, defibrillation electrode 24 may be a flat ribbon electrode, paddle electrode, braided or woven electrode, mesh electrode, segmented electrode, directional electrode, patch electrode or other type of electrode besides an elongated coil electrode. In one example, defibrillation electrode 24 may be formed of a first segment and a second segment separated by a distance and having an electrode or a pair of electrodes (such as electrode 28 and/or 30 described below) located between the first and second defibrillation electrode segments. In one example, the segments may be coupled to the same conductor within the lead body such that the first and second segments function as a single defibrillation electrode. In other embodiments, defibrillation lead 16 may include more than one defibrillation electrode. For example, the first and second segments described above may be coupled to different conductors within the lead body such that the first and second segments function as separate defibrillation electrodes along the distal portion of lead 16. As another example, defibrillation lead 16 may include a second defibrillation electrode (e.g., second elongated coil electrode) near a proximal end of lead 16 or near a middle portion of lead 16.

Lead 16 also includes electrodes 28 and 30 located along the distal portion of lead 16. In the example illustrated in FIGS. 1A-C, electrode 28 and 30 are separated from one another by defibrillation electrode 24. In other examples, however, electrodes 28 and 30 may be both distal of defibrillation electrode 24 or both proximal of defibrillation electrode 24. In instances in which defibrillation electrode 24 is a segmented electrode with two defibrillation segments, electrodes 28 and 30 may be located between the two segments. Alternatively, one of electrodes 28 and 30 may be located between the two segments with the other electrode located proximal or distal to defibrillation electrode 24. Electrodes 28 and 30 may comprise ring electrodes, short coil electrodes, hemispherical electrodes, segmented electrodes, directional electrodes, or the like. Electrodes 28 and 30 of lead 16 may have substantially the same outer diameter as the lead body. In one example, electrodes 28 and 30 may have surface areas between 1.6-55 mm$^2$. Electrodes 28 and 30 may, in some instances, have relatively the same surface area or different surface areas. Depending on the configuration of lead 16, electrodes 28 and 30 may be spaced apart by the length of defibrillation electrode 24 plus some insulated length on each side of defibrillation electrode, e.g., approximately 2-16 cm. In other instances, such as when electrodes 28 and 30 are between a segmented defibrillation electrode, the electrode spacing may be smaller, e.g., less than 2 cm or less the 1 cm. The example dimensions provided above are exemplary in nature and should not be considered limiting of the embodiments described herein. In other examples, lead 16 may include a single pace/sense electrode or more than two pace/sense electrodes.

In some instances, electrodes 28 and 30 of lead 16 may be shaped, oriented, designed or otherwise configured to reduce extracardiac stimulation. For example, electrodes 28 and 30 of lead 16 may be shaped, oriented, designed or otherwise configured to focus, direct or point electrodes 28 and 30 toward heart 26. In this manner, pacing pulses delivered via lead 16 are directed toward heart 26 and not outward toward skeletal muscle. For example, electrodes 28 and 30 of lead 16 may be partially coated or masked with a polymer (e.g., polyurethane) or another coating material (e.g., tantalum pentoxide) on one side or in different regions so as to direct the pacing signal toward heart 26 and not outward toward skeletal muscle.

ICD 14 may obtain sensed electrical signals corresponding with electrical activity of heart 26 via a combination of sensing vectors that include combinations of electrodes 28 and/or 30 and the housing electrode of ICD 14. For example, ICD 14 may obtain electrical signals sensed using a sensing vector between electrodes 28 and 30, obtain electrical signals sensed using a sensing vector between electrode 28 and the conductive housing electrode of ICD 14, obtain electrical signals sensed using a sensing vector between electrode 30 and the conductive housing electrode of ICD 14, or a combination thereof. In some instances, ICD 14 may even obtain sensed electrical signals using a sensing vector that includes defibrillation electrode 24.

ICD 14 analyzes the sensed electrical signals obtained from one or more of the sensing vectors of lead 16 to monitor for tachyarrhythmia, such as ventricular tachycardia or ventricular fibrillation. ICD 14 generates and delivers substernal electrical stimulation therapy, e.g., ATP, cardioversion or defibrillation shocks, and/or post-shock pacing in response to detecting tachycardia (e.g., VT or VF). In some instances, ICD 14 may generate and deliver bradycardia pacing in addition to ATP, cardioversion or defibrillation shocks, and/or post-shock pacing.

Although system 10 of FIG. 1 is illustrated as having a distal portion of lead 16 implanted within the substernal space of patient 12, the implant tools and techniques of this disclosure may be used to implant leads at other locations. In one example, the implant tools and techniques may be utilized to implant the lead 16 subcutaneously above the sternum and/or ribcage of patient 12. In another example, the implant tools and techniques may be utilized to implant lead 16 at a pericardial or epicardial location.

In the example illustrated in FIG. 1, system 10 is an ICD system that provides cardioversion/defibrillation and/or pacing therapy. However, the implant tools and techniques may be utilized to implant other types of implantable medical leads, catheters (e.g., drug delivery catheters), or other implantable component or assembly. In addition, it should be noted that system 10 may not be limited to treatment of a human patient. In alternative examples, system 10 may be implemented in non-human patients, e.g., primates, canines, equines, pigs, ovines, bovines, and felines. These other animals may undergo clinical or research therapies that may benefit from the subject matter of this disclosure.

FIG. 2 is a conceptual drawing illustrating an example tunneling tool. The tunneling tool 40 may be used to implant a medical lead, such as lead 16 of FIG. 1, a catheter, or other implantable component. The tunneling tool 40 includes a shaft 42 and a handle 44. As will be described in further detail herein, the tunneling tool 40 of FIG. 2 may be particularly useful in implanting medical lead 16 such that a distal end of medical lead 16 is located in the substernal space.

Shaft 42 includes a proximal segment 46 that is permanently coupled to the handle and a distal segment 48 that is detachably coupled to proximal segment 46. FIG. 2 illustrates the configuration in which distal segment 48 is detached from proximal segment 46. As described further herein, however, distal segment 48 may be connected to proximal segment 46 to form a single shaft.

Figure 3A:
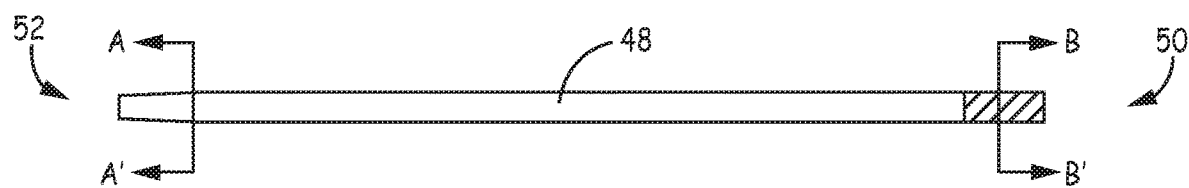
FIGS. 3A-C are conceptual drawing illustrating various views of a distal segment of the tunneling too of FIG. 2.
Figure 3B:
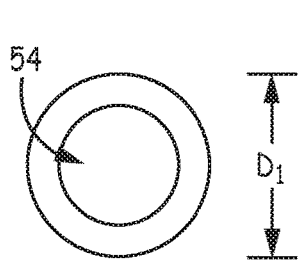
Figure 3C:
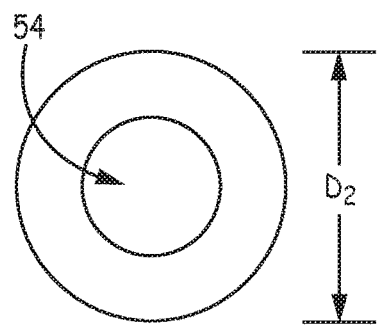

Distal segment 48 is illustrated in FIGS. 3A-C. Distal segment 48 has a length (L1) extending from a proximal end 50 and a distal end 52. The length L1 may be between approximately one inch and seven inches. However, length L of distal segment 48 may be less than one inch and greater than six inches without departing from the scope of this disclosure. In some instances, distal segment 48 is tapered along at least a portion of the length L1 from proximal end 50 to distal end 52. In particular, an outer diameter (D1) of distal end 52 of distal segment 48 is smaller than an outer diameter (D2) of the proximal end 50 of distal segment 48. In other instances, distal segment 48 may not have a taper. As will be described in further detail herein, a tapered distal segment dilates the tunnel through the diaphragmatic attachments and/or subcutaneous tunnel. The distal end 52 of distal segment 48 may be blunt, rounded, tapered, pointed or otherwise shaped reduce damage to surrounding tissue, piercing of organs, or coring of the tissue, muscles, ligaments or other features in the path.

Distal segment 48 includes a lumen 54 that extends the entire length L from proximal end 50 to distal end 52. Lumen 54 may be sized (e.g., have a diameter) to receive a needle or other puncturing element. For example, lumen 54 may have a diameter sized to receive a 15-22 gauge needle, and thus have a diameter between approximately 0.7 millimeters (mm) and 2 mm. The needle or other puncturing element may be placed through lumen 54 of distal segment 48 either before or after the needle or other puncturing element punctures through the diaphragmatic attachments.

Proximal segment 46 of shaft 42 may be permanently attached to handle 44. Proximal segment 46 may extend from handle to a distal end 56 to form a length L2. Length L2 of proximal segment 46 may be between approximately two inches to sixteen inches depending on the length of distal segment 48 and the overall desired length of tool 40. However, proximal segment 46 may be shorter than 2 inches or longer than sixteen inches without departing from the scope of this disclosure. Proximal segment 46 may include a lumen that extends along a substantial portion of length L2 of proximal segment 46. When attached to distal segment 48, lumen 54 and the lumen of proximal segment 46 would connect such that a fluid could be delivered from the proximal end of shaft 42 adjacent to handle 44 through proximal segment 46 and out distal end 52 of distal segment 48. In other instances, proximal segment may not have a lumen extending along a substantial portion of length L2.

Proximal segment 46 and distal segment 48 may be constructed of any of a variety of materials. In some instances, proximal segment 46 and distal segment 48 may be formed from the same material, e.g., metal or polymer. In other instances, proximal segment 46 and distal segment 48 may be formed from different materials. For example, the proximal segment 46 may be constructed of a metal and the distal segment may be constructed of a polymer. In some instances, distal segment 48 may be constructed of both metal (or metal alloy) and polymer. For example, proximal end 50 of distal segment 48 may be formed of metal and distal end 52 of distal segment 48 may be formed of a polymer. The metal may include, but not be limited to, stainless steel, aluminum, tantalum, MP35N, precious metals, other metals or metal alloys. The polymer may include, but not be limited to, be one or more of PEEK, PEKK, silicone, urethane, Pebax, polyethylene, acetal, or other polymer or combination of polymers. In some instances, segments 46 and 48 may be made of a blend of metal and polymer, e.g., platinum-cured silicone or polymers with metal fillers, metal-braided polymers, and/or a polymer coated with a coating, e.g., hydrophilic coating, to improve lubriciousness. Handle 44 may also be constructed of any of the metal, metal alloy, polymer, blended metal/polymer, or metal-braided polymers described above. In some instances, distal segment 48 may be formed of a radiopaque material and/or radiopaque rings or other features may be added to distal segment 48.

In some instances, proximal segment 46 and/or distal segment 48 may be malleable. For example, a user of tool 30 may form shaft 42 to achieve a desired shape or bend by manipulating one or both of proximal segment 46 and/or distal segment 48. In other instances, proximal segment 46 and/or distal segment 48 may pre-formed or pre-shaped. In either case, the bend or curvature of shaft 42 (whether pre-formed or not) may be particularly useful for tunneling underneath/below the sternum. In particular, the bend or curvature of shaft 42 orients the distal end 52 toward sternum thereby keeping distal end 52 away from organs in the body cavity during tunneling through the substernal space.

Proximal segment 46 and distal segment 48 may be detachably coupled via any of a number of connection mechanisms. In one example, distal end 56 of proximal segment 46 may have a diameter that is less than proximal end 50 of distal segment 48 and have an external thread while proximal end 50 of distal segment 48 may have an internal thread. In this example, proximal segment 46 and distal segment 48 may be attached to one another by screwing them together. However, any detachable connection mechanism may be used to couple segments 46 and 48. Other possible connection mechanisms include, without limitation, an internal locking mechanism or cavity inside of one segment and a pin or other protrusion in the other that mates with the locking mechanism or cavity. As another example, the connection may be a type of plug and receptacle connection. In another example, the two pieces could be connected via an external piece, e.g., via set screw(s).

In some instances, the tunneling tool 40 may be used in conjunction with a sheath 60, an example of which is illustrated in FIG. 4. Sheath 60 includes a body 62 and a handle 64. Body 62 of sheath 60 defines an inner channel. In one example, sheath 60 may be an open sheath as illustrated and described in U.S. patent application Ser. No. 14/196,298 and U.S. patent application Ser. No. 14/196,443, both of which are incorporated herein by reference in their entireties. In the case of an open sheath, sheath 60 may include an opening along the length of body 62 and the inner channel is accessible via the opening anywhere along the length of body 62. In another example, sheath 60 may be a splittable sheath in which body 62 includes a score or other weakened portion to permit splitting of body 62, e.g., as illustrated and described in further detail in U.S. patent application Ser. No. 14/196,443, previously incorporated above. In yet another example, sheath 60 may be a sheath without any gap or score on body 62, in which case sheath 60 may be removed by slitting the sheath using a slitter, as illustrated and described U.S. patent application Ser. No. 14/196,443, previously incorporated above.

Sheath 60 may have a length that is less than or equal to the length L2 of proximal segment 46 of shaft 42. In the case of an open sheath, however, the length of sheath 60 may be longer than the length L2 of proximal segment 46 given that sheath 60 may be placed on shaft 42 after connecting proximal segment 46 to distal segment 48. Sheath 60 may have other properties describe above in reference to U.S. patent application Ser. No. 14/196,298 and U.S. patent application Ser. No. 14/196,443 or any commercially available sheaths.

Figure 5:
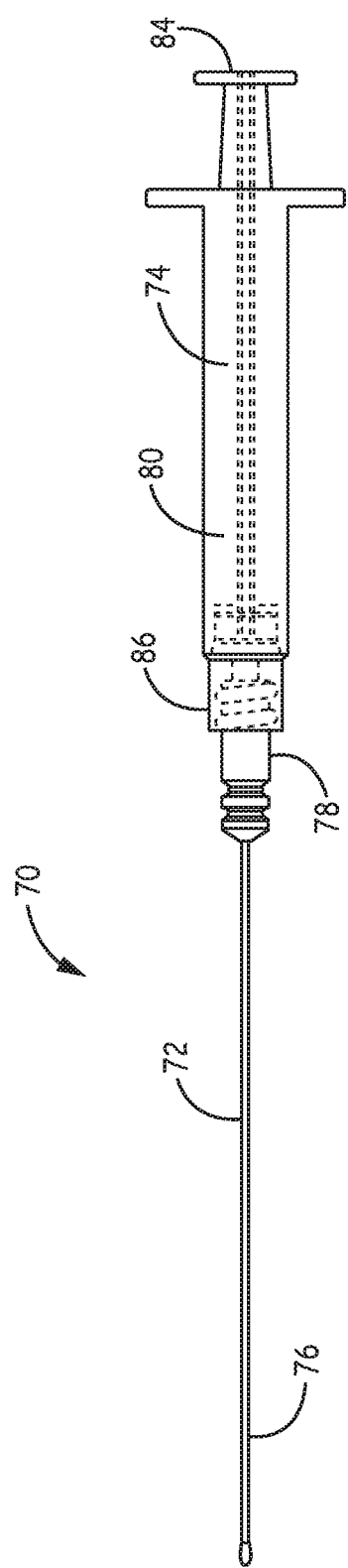
FIG. 5 is a conceptual diagram illustrating an example puncture tool that includes a needle connected to a syringe and that may be used in conjunction with the tunneling tool of FIG. 2 to implant the medical lead, catheter or other implantable component.

FIG. 5 is a conceptual diagram illustrating an example puncture tool 70. In the example illustrated in FIG. 5, puncture tool 70 that includes a needle 72 connected to a syringe 74. In one example, needle 72 includes a cannula 76 and a fitting 78. Cannula 76 may include a blunt back (proximal) end and a pointed (distal) end. The pointed end of cannula 76 may include any of a number of point styles including, but not limited to, a bevel point. Cannula 76 may be formed of stainless steel or other suitable material. In some instances, needle 72 may not be a hollow cannula 76. Instead, needle 72 may be a solid needle. Needle 72 may be any of a number of diameters, e.g., between 15-gauge and 22 gauge, and any of a number of lengths, e.g., 1-6 inches.

The blunt back (proximal) end of the cannula 76 may be coupled to fitting 78. In some instances, cannula 76 may be permanently coupled to fitting 78. In other instances, cannula 76 may be removably coupled to fitting 78. At the end of fitting 78 opposite of the end coupled to cannula 76, fitting 78 may be threaded (internal or external), Luer lock connection, slip tip connection, or other appropriate connection mechanism for coupling the fitting 78 of needle 72 to the syringe 74. Fitting 78 may be made of stainless steel, brass, plated brass, plastic or other suitable material.

Syringe 74 includes a tube 80 that includes an open end 82 and a plunger 84 that fits within tube 80. Plunger 84 may be pulled or pushed along the inside of tube 80 allowing syringe 74 to take in and eject a liquid or gas through open end 82. Open end 82 of syringe 74 may be fitted with tip connector 86 configured to couple with fitting 78 of needle 72. Connector 86 may be a Luer lock connector, slip tip connector or other connection mechanism. In one example, connector 86 of syringe 74 is a male Luer connector and fitting 78 of needle 72 is a female Luer connector.

Although the puncture tool illustrated in FIG. 5 is comprised of needle 72 and syringe 74, needle 72 may be connected to other types of handles besides a syringe. In some instances, needle 72 does not connect to a syringe or other handle. Instead, needle 72 may include wings or other mechanism that may be used as a built-in handle to advance the needle through the fibrous/ligamentous diaphragmatic attachments.

The delivery tools and/or systems described herein may be used to implant medical leads, catheters, or other implantable component. In one example, the delivery tools and/or systems described herein may be used to implant a medical electrical lead at least partially within a substernal location. The delivery tools may be used in multiple different manners, thus providing physicians with a single tool that is useful in multiple implant techniques.

In a first possible use, an implanter may implant the distal portion of lead 16 underneath the sternum by traversing the diaphragmatic attachments near the xiphoid process using puncturing tool 70, e.g., by pushing needle 72 through the diaphragmatic attachments near the xiphoid process. In some instances, the distal segment 48 of shaft 42 may be placed onto needle 72 prior to pushing needle 72 through the diaphragmatic attachments. In other words, needle 72 may extend through lumen 54 of distal segment 48. In other instances in which the cannula 76 is removable from fitting 78, distal segment 48 may be slid over needle 72 after pushing needle 72 through the diaphragmatic attachments.

In either case, after crossing the diaphragmatic attachments with needle 72, needle 72 is removed from the patient while leaving distal segment 48 in place, e.g., distal end 52 within the body and through diaphragmatic attachments and proximal end 50 extending out of the body. Distal segment 48 is coupled to proximal segment 46 of tunneling tool 40. Tunneling tool 40 may now be used as a tunneling rod to tunnel the distal segment 48 superior along the underside of the sternum.

Prior to tunneling along the underside of the sternum, sheath 60 may be placed over shaft 42. In one example, sheath 60 is sized to be less than the length of the proximal segment 46 of shaft 42. In this case, sheath 60 may be placed onto the proximal segment 46 prior to coupling proximal segment 46 to distal segment 48. In another example, sheath 60 may be an open sheath having a length greater than that of proximal segment 46. In this case, sheath 60 may be placed onto shaft 42 via the opening of the sheath after coupling proximal segment 46 to distal segment 48.

After tunneling to a desired location, tunneling tool 40 is removed from the body while leaving sheath 60 in place along the posterior side of the sternum. The distal end of lead 16 is pushed through sheath 60. Sheath 60 is then removed leaving the distal portion of lead 60 in place along the posterior side of the sternum. Tunneling tool 40, with proximal segment 46 and distal segment 48 connected, and sheath 60 (or another sheath) may then be used to form a subcutaneous tunnel lateral from the center of the torso of the patient to a pocket on the left side of the patient. The tunneling tool 40 may be removed leaving sheath 60 in place and the proximal end of lead 16 may be pushed through sheath 60. Sheath 60 may be removed leaving the proximal portion of lead 16 in place along the lateral path. The connector of lead 16 may be connected to the ICD.

In other instances, tunneling tool 40 and sheath 60 may be used to traverse the diaphragmatic attachments near the xiphoid process without the use of a puncturing tool 70. In this case, proximal portion 46 and distal portion 48 are coupled at all points in the procedure.

As described above, the implant tools and techniques described herein may be utilized to implant lead 16 at locations other than within the substernal space. The implant tools and techniques may be utilized to implant lead 16 at a pericardial or epicardial location, for instance. For example, the same techniques may be used to traverse the diaphragmatic attachments in a pericardial or epicardial implant procedure. In other examples, the implant tools and techniques may be used to enter into the pericardial space or the epicardium. For instance, the needle may be inserted into the pericardial space (e.g., through the sac), the distal segment may be slid over the needle and into the pericardial or epicardial space. The needle may then be removed and the distal segment coupled to the proximal segment for tunneling/routing the distal end of the tunneling tool.

Various examples have been described. These and other examples are within the scope of the following claims.

The invention claimed is:

1. An implant tool comprising: a tunneling tool that includes: a handle; and a shaft that includes: a proximal segment that is permanently fixed to the handle, the proximal segment including a proximal end fixed to the handle and a distal end, and a distal segment that is detachably coupled to the proximal segment, the distal segment including a proximal end configured to couple to the proximal segment, a distal end, and a lumen extending an entire length of the distal segment from the proximal end of the distal segment to the distal end of the distal segment, wherein the shaft is configured to tunnel within a patient, a puncturing tool having a proximal end and a distal end, wherein the distal end of the puncturing tool is sharp, the puncturing tool sized to fit through the lumen extending the length of the distal segment of the shaft; and a sheath configured to be placed over the shaft, wherein a length of the sheath is less than a length of the proximal segment of the shaft, wherein the implant tool is configured such that, when the sheath is placed over the proximal segment of the shaft, the distal end of the sheath is proximal to the distal end of the proximal segment, wherein the tunneling tool is configured such that, when the distal segment is detachably coupled to the proximal segment, movement of the handle in a distal direction along a longitudinal axis defined by the shaft causes movement of the proximal segment and the distal segment in the distal direction, wherein the proximal end of the distal segment has a first outer diameter and the distal end of the distal segment has a second outer diameter, and the first outer diameter and the second outer diameter are different, wherein the distal segment is tapered between the proximal end of the distal segment having the first outer diameter and the distal end of the distal segment having the second outer diameter, and wherein the distal segment detachably couples to the proximal segment without the puncturing tool in the lumen of the distal segment.

2. The implant tool of claim 1, wherein the distal segment of the shaft is between approximately one inch and seven inches in length and the proximal segment of the shaft is between approximately two inches and sixteen inches in length.

3. The implant tool of claim 1, wherein the distal segment of the shaft is made from a first material and the proximal segment of the shaft is made from a second material, the first material being different from the second material.

4. The implant tool of claim 3, wherein the first material comprises a polymer.

5. The implant tool of claim 3, wherein the first material of the distal segment and the second material of the proximal segment comprise a metal or a metal alloy.

6. The implant tool of claim 1, wherein the proximal segment of the shaft forms a lumen that extends along substantially an entire length of the proximal segment.

7. The implant tool of claim 1, wherein the distal end of the distal segment of the shaft is blunt.

8. The implant tool of claim 1, wherein at least a portion of the distal segment of the shaft is radiopaque.

9. The implant tool of claim 1, wherein the proximal end of the distal segment and the distal end of the proximal segment form a threaded connection to each other that detachably couples the distal end of the proximal segment to the proximal end of the distal segment.

10. The implant tool of claim 1, wherein the puncturing tool comprises a needle.

11. The implant tool of claim 10, wherein the puncturing tool further comprises a syringe coupled to the needle.

12. The implant tool of claim 1, wherein the tunneling tool is configured to tunnel along the posterior side of the sternum.

13. The implant tool of claim 1, wherein the distal segment is malleable such that the distal segment is bendable from a substantially straight configuration to a curved configuration between the proximal end and distal end of the distal segment.

14. The implant tool of claim 1, wherein the distal segment exhibits a curvature in the distal direction.

15. The implant tool of claim 1, wherein an outer diameter along the length of the distal segment is tapered such that the outer diameter increases moving proximally along the distal segment and beginning at the distal end of the distal segment.

16. The implant tool of claim 15, wherein the outer diameter along the length of the distal segment is tapered along only a portion of the distal segment.

17. The implant tool of claim 1, wherein the distal segment is formed of a unitary segment.

18. The implant tool of claim 1, wherein the distal segment is tapered such that there is only a single tapered portion of the distal segment.

19. The implant tool of claim 1, wherein the shaft has a preformed curvature relative to a longitudinal axis of the handle.

20. An implant tool comprising: a tunneling tool that includes: a handle; and a shaft that includes: a proximal segment that is permanently fixed to the handle, the proximal segment including a proximal end fixed to the handle and a distal end, and a distal segment that is detachably coupled to the proximal segment, the distal segment including a proximal end configured to couple to the proximal segment, a distal end, and a lumen extending an entire length of the distal segment from the proximal end of the distal segment to the distal end of the distal segment, wherein the shaft is configured to tunnel within a patient, a puncturing tool having a proximal end and a distal end, wherein the distal end of the puncturing tool is sharp, the puncturing tool sized to fit through the lumen extending the length of the distal segment of the shaft; and a sheath configured to be placed over the shaft, wherein a length of the sheath is less than a length of the proximal segment of the shaft, wherein the implant tool is configured such that, when the sheath is placed over the proximal segment of the shaft, the distal end of the sheath is proximal to the distal end of the proximal segment, and wherein the distal segment of the shaft is made from a first material and the proximal segment of the shaft is made from a second material, the first material being different from the second material.

21. The implant tool of claim 20, wherein the first material of the distal segment is malleable such that the distal segment is bendable from a substantially straight configuration to a curved configuration between the proximal end and distal end of the distal segment.

22. An implant tool comprising: a tunneling tool that includes: a handle; and a shaft that includes: a proximal segment that is permanently coupled to the handle, the proximal segment including a proximal end fixed to the handle and a distal end, and a distal segment that is detachably coupled to the proximal segment, the distal segment including a proximal end configured to couple to the proximal segment, a distal end, and a lumen extending an entire length of the distal segment from the proximal end of the distal segment to the distal end of the distal segment, wherein the shaft is configured to tunnel within a patient, a puncturing tool having a proximal end and a distal end, wherein the distal end of the puncturing tool is sharp, the puncturing tool sized to fit through the lumen extending the length of the distal segment of the shaft; and a sheath configured to be placed over the shaft, wherein a length of the sheath is less than a length of the proximal segment of the shaft, wherein the implant tool is configured such that, when the sheath is placed over the proximal segment of the shaft, the distal end of the sheath is proximal to the distal end of the proximal segment, and wherein the proximal end of the distal segment and the distal end of the proximal segment form a threaded connection to each other that detachably couples the distal end of the proximal segment to the proximal end of the distal segment without the puncturing tool in the lumen of the distal segment.

* * * * *